United States Patent
Bailey et al.

(10) Patent No.: US 10,464,871 B2
(45) Date of Patent: *Nov. 5, 2019

(54) PROCESS FOR THE PRODUCTION OF ETHANOL BY HYDROGENATION OF METHYL ACETATE

(71) Applicant: BP P.L.C., London (GB)

(72) Inventors: Craig Bailey, East Yorkshire (GB); Leslie William Bolton, Middlesex (GB)

(73) Assignee: BP P.L.C., London (GB)

( * ) Notice: Subject to any disclaimer, the term of this patent is extended or adjusted under 35 U.S.C. 154(b) by 127 days.

This patent is subject to a terminal disclaimer.

(21) Appl. No.: 15/107,779

(22) PCT Filed: Dec. 19, 2014

(86) PCT No.: PCT/EP2014/078723
§ 371 (c)(1),
(2) Date: Jun. 23, 2016

(87) PCT Pub. No.: WO2015/097086
PCT Pub. Date: Jul. 2, 2015

(65) Prior Publication Data
US 2016/0326074 A1 Nov. 10, 2016

(30) Foreign Application Priority Data

Dec. 24, 2013 (EP) .................................. 13199526
Jun. 19, 2014 (GB) .................................. 1410930.0

(51) Int. Cl.
C07C 29/149 (2006.01)
C07C 29/82 (2006.01)
C07C 67/08 (2006.01)

(52) U.S. Cl.
CPC .......... C07C 29/149 (2013.01); C07C 29/82 (2013.01); C07C 67/08 (2013.01); *Y02P 20/582* (2015.11)

(58) Field of Classification Search
CPC ........ C07C 29/82; C07C 29/149; C07C 67/08
See application file for complete search history.

(56) References Cited

U.S. PATENT DOCUMENTS

| 3,772,380 A | 11/1973 | Paulik et al. |
| 4,497,967 A * | 2/1985 | Wan ................. C07C 29/149 560/265 |
| 5,625,094 A | 4/1997 | Nobel et al. |
| 2011/0306805 A1* | 12/2011 | Daniel ............... C07C 29/149 568/885 |

FOREIGN PATENT DOCUMENTS

| DE | 1 767 150 | 3/1972 |
| EP | 0 060 719 A1 | 9/1982 |
| EP | 0087070 | 8/1983 |
| EP | 0 616 997 A1 | 9/1994 |
| EP | 0618184 | 10/1994 |
| EP | 0657386 | 6/1995 |
| GB | 1 234 121 | 6/1971 |
| GB | 1 468 940 | 3/1977 |
| GB | 1 538 783 | 1/1979 |
| WO | WO 2009/063173 A1 | 5/2009 |
| WO | WO 2012/062633 A1 | 5/2012 |

* cited by examiner

*Primary Examiner* — Yate' K Cutliff
(74) *Attorney, Agent, or Firm* — McDonnell Boehnen Hulbert & Berghoff LLP

(57) ABSTRACT

Process for the production of ethanol from acetic acid and hydrogen, said process comprising: reacting in an esterification reaction vessel methanol with acetic acid in the presence of an esterification catalyst and an entrainer to form a product comprising entrainer, methyl acetate and water, and in a distillation column, recovering from the product an overhead product fraction comprising methyl acetate, methanol and water, feeding the overhead product fraction, together with hydrogen, into a hydrogenation unit containing a copper based hydrogenation catalyst, to produce a hydrogenation product stream comprising ethanol, methanol, unreacted methyl acetate, unreacted hydrogen, ethyl acetate and water, cooling the hydrogenation product stream; separating the cooled hydrogenation product stream into a liquid phase which comprises the majority of the methanol, ethanol, methyl acetate, ethyl acetate and water, and a gaseous phase which comprises the majority of the unreacted hydrogen; recycling at least part of the gaseous phase to the hydrogenation unit; separating a lower boiling product stream comprising methanol, methyl acetate and ethyl acetate, and a higher boiling product stream comprising ethanol, water, from the liquid phase; recycling at least part of the lower boiling product stream to the esterification reaction vessel; and, optionally removing water from the higher boiling product stream.

23 Claims, No Drawings

PROCESS FOR THE PRODUCTION OF ETHANOL BY HYDROGENATION OF METHYL ACETATE

This application is the U.S. national phase of International Application No. PCT/EP2014/078723 filed Dec. 19, 2014 which designated the U.S. and claims priority to European Patent Application No. 13199526.8 filed Dec. 24, 2013, and British Patent Application No. 1410930.0 filed Jun. 19, 2014, the entire contents of each of which are hereby incorporated by reference.

The present invention relates to process for the production of ethanol. In particular, the present invention relates to a process for the production of ethanol from acetic acid and hydrogen, said ethanol being produced via the esterification of acetic acid with methanol to form methyl acetate followed by the hydrogenation of methyl acetate to form ethanol and methanol.

In recent years, increased use and demand for ethanol has led to a greater interest in processes relating to the production of ethanol.

Many methods for the production of ethanol from a variety of feedstocks are known in the art. For instance, processes for the preparation of ethanol via fermentation processes, in particular by the fermentation of biomass, are well known. The term "biomass" as used herein refers to any source of organic material from biological origin. Examples of fermentation processes include the direct fermentation of biomass, such as sources of a carbohydrate, to ethanol, as well as the fermentation of derivatives of biomass to ethanol. For instance, bioethanol may be obtained by fermentation of feedstocks derived from sugar cane, such as sugar cane molasses and sugar cane juice; sugar beet, such as sugar beet molasses and sugar beet juice; cereal crops, such as corn or wheat, and cereal crop derived feedstocks, such as corn syrup; and lignocellulosic materials, such as fast growing grasses or "energy grasses". Alternative methods for the preparation of ethanol via fermentation processes include the preparation of ethanol by fermentation process performed on a feed stream comprising carbon monoxide and hydrogen, such as synthesis gas; such processes are referenced and described in WO 2012/062633 A1.

Methods for the thermochemical preparation of ethanol are also well known in the art and such methods include the direst synthesis of alcohols from synthesis gas, the preparation of alcohols by the hydrogenation of carboxylic acids and/or esters thereof, and the hydration of alkenes.

WO 2009/063173 A1 discloses a process for the production of ethanol from ethanoic acid and $H_2$, characterised by the following steps:

(1) introducing ethanoic acid, together with methanol and/or ethanol into an esterification reactor to produce methyl ethanoate and/or ethyl ethanoate, (2) introducing ethanoate from step 1, together with $H_2$ and water, into a hydrogenation unit to produce a stream comprising ethanol, unreacted ethanoate and optionally methanol, (3) separating the resulting stream, from step 2, into unreacted ethanoate and ethanol and optionally methanol, (4) optionally reintroducing ethanoate, from step 3, into the esterification reactor of step 1, (5) using at least a part of the methanol and/or the ethanol of step 3, as the methanol and/or ethanol feed of the esterification reactor of step 1, and (6) recovering ethanol, from step 3.

EP0060719B1 discloses a process for the production of methyl acetate which process comprises reacting in an esterification reaction vessel methanol at elevated temperature with acetic acid in the presence of an esterification catalyst and an entrainer which is sparingly soluble in water and which forms a minimum boiling point azeotrope therewith to form a product comprising entrainer, methyl acetate and water, and in a distillation column, recovering from the product an overhead fraction comprising methyl acetate characterised in that from an intermediate point in the column there is removed a liquid sidestream fraction comprising water and entrainer.

There remains a need in the art to provide an improved and/or optimised process for the preparation of ethanol from acetic acid. Such improvements and/or optimisation may be obtained by the increased simplification of the process, the increased integration of the steps of the process, a reduction in the amount of energy required in the process, an increase productivity of the process, an increased selectivity of the process to ethanol, a reduction in the amount of by-products formed in the process, or any combination thereof.

The present invention provides a process for the production of ethanol from acetic acid and hydrogen, said process comprising the following steps:

(1) reacting in an esterification reaction vessel methanol at elevated temperature with acetic acid in the presence of an esterification catalyst and an entrainer which is sparingly soluble in water and which forms a minimum boiling point azeotrope therewith to form a product comprising entrainer, methyl acetate and water, and in a distillation column, recovering from the product an overhead product fraction comprising methyl acetate, methanol and water, and from an intermediate point in the column removing a liquid sidestream fraction comprising water, methanol, entrainer and methyl acetate, wherein the molar ratio of acetic acid to methanol in the esterification reaction vessel is in the range of from 1:1.1 to 1:1.8, preferably in the range of from 1:1.2 to 1:1.6, and the distillation column is operated at an overall pressure of at most 5 bara, preferably at most 3 bara, more preferably at most 2 bara, and wherein the amount of water present in the overhead product fraction comprising methyl acetate, methanol and water is in the range of from 0.5 to 5 mol %;

(2) feeding the overhead product fraction comprising methyl acetate, methanol and water from step 1, together with hydrogen, into a hydrogenation unit containing a copper based hydrogenation catalyst, wherein said hydrogenation unit is operated in the vapour phase at elevated temperature, preferably at a temperature in the range of from 180 to 270° C., and elevated pressure, preferably in the range of from 20 to 100 bara, to produce a hydrogenation product stream comprising ethanol, methanol, unreacted methyl acetate, unreacted hydrogen, ethyl acetate and water, wherein the total molar ratio of hydrogen to methyl acetate in the hydrogenation unit is in the range of from 5:1 to 20:1;

(3) cooling the hydrogenation product stream from step 2 to a temperature below 120° C., preferably to a temperature below 80° C., and a pressure which is no more than 10 bar lower than the pressure of the hydrogenation unit, preferably no more than 5 bar lower than the pressure of the hydrogenation unit, such that the majority of the methanol, ethanol, methyl acetate, ethyl acetate and water present in the hydrogenation product stream condense;

(4) separating the cooled hydrogenation product stream from step 3 into a liquid phase which comprises the majority of the methanol, ethanol, methyl acetate, ethyl acetate and water, and a gaseous phase which comprises the majority of the unreacted hydrogen;

(5) recycling at least part of the gaseous phase from step 4, preferably at least 80 vol. % of the gaseous phase from step 4, more preferably at least 90 vol. % of the gaseous phase from step 4, most preferably at least 95 vol. % of the gaseous phase from step 4, to the hydrogenation unit of step 2;

(6) separating a lower boiling product stream comprising methanol, methyl acetate and ethyl acetate, and a higher boiling product stream comprising ethanol, water, from the liquid phase of step 4 in a distillation column operated at an overall pressure of at most 5 bara, preferably at most 3 bara;

(7) recycling at least part of the lower boiling product stream from step 6, preferably at least 80 vol. % of the lower boiling product stream from step 6, more preferably at least 90 vol. % of the lower boiling product stream from step 6, most preferably at least 95 vol. % of the lower boiling product stream from step 6, to the esterification reaction vessel of step 1; and (8) optionally removing water from the higher boiling product stream of step 6.

The process of the present invention provides a process for the manufacture of ethanol from acetic acid and hydrogen via the formation of a methyl acetate intermediate.

In step 1 of the process of the present invention, methanol and acetic acid are reacted at elevated temperature in an esterification reaction vessel in the presence of an esterification catalyst and an entrainer which is sparingly soluble in water and which forms a minimum boiling point azeotrope therewith to form a product comprising entrainer, methyl acetate and water, and in a distillation column, an overhead product fraction is recovered from the product comprising methyl acetate, methanol and water, and from an intermediate point in the column a liquid sidestream fraction comprising water, methanol, entrainer and methyl acetate is removed, wherein the molar ratio of acetic acid to methanol in the esterification reaction vessel is in the range of from 1:1.1 to 1:1.8, and the distillation column is operated at an overall pressure of at most 5 bara, and wherein the amount of water present in the overhead product fraction comprising methyl acetate, methanol and water is in the range of from 0.5 to 5 mol %.

The entrainer may suitably be added to the esterification reaction vessel or to a suitable point in the distillation column.

The process of the present invention may be operated batchwise or continuously, preferably continuously. Likewise, step 1 of the process of the present invention may be operated batchwise or continuously, preferably continuously.

In a preferred embodiment of the present invention, the methanol and acetic acid are continuously fed to the esterification reaction vessel containing entrainer, methanol, acetic acid and esterification catalyst to produce a product comprising entrainer, unreacted methanol, methyl acetate and water, distilling from the product in a distillation column an overhead product fraction comprising methyl acetate, methanol and water, removing from the intermediate point in the column a liquid sidestream fraction comprising water, methanol, entrainer and methyl acetate, separating a fraction comprising the majority of the methanol, entrainer and methyl acetate, from the water and returning said separated fraction to a point in the distillation column of step 1 which is lower than the sidestream removal point.

The esterification reaction vessel may be separate from the distillation column of step 1 or integrated therewith. Preferably, the esterification reaction vessel is a kettle at the base of the distillation column, which suitably may contain not less than 8 theoretical stages and preferably from 15 to 50 theoretical stages. Whenever the esterification reaction vessel is separate from the distillation column of step 1, it is preferred to recycle the residue from the base of the distillation column to the esterification reaction vessel.

The molar ratio of acetic acid to methanol in the esterification reaction vessel is in the range of from 1:1.1 to 1:1.8, preferably, the molar ratio of acetic acid to methanol in the esterification reaction vessel is in the range of from 1:1.2 to 1:1.6.

The molar ratio of acetic acid to methanol in the esterification reaction vessel has to be maintained within a suitable range to control the amount of water that is present in the overhead product fraction. Whilst not wishing to be bound by theory, the overhead fraction from the distillation column of step 1 will consist of the lowest boiling fractions present in the distillation column, and will typically comprise an intermediate composition between the azeotropes of methyl acetate/water and methyl acetate/methanol. Increasing the methanol excess will increase the proportion of the overhead fraction that is made up of the methyl acetate/methanol azeotrope and therefore reduce the amount of water present in the overhead product fraction. Due to the presence of ethyl acetate in the lower boiling product stream of step 6, ethyl acetate would also be present in the esterification reaction vessel of step 1 through the recycling of step 7. The ethyl acetate present in the esterification reaction vessel would also form an ethyl acetate/water azeotrope that would be present in the overhead product fraction. Due to the relatively greater amount of water present in the ethyl acetate/water azeotrope compared to the methyl acetate/water azeotrope, the amount of methanol required in the esterification reaction vessel in order to maintain the optimal amount of water in the overhead product fraction would increase with increasing amounts of ethyl acetate in the lower boiling product stream of step 6.

The elevated temperature of the esterification reaction in step 1 may vary over a moderately wide range, but must be sufficient, in the embodiment wherein the esterification reaction vessel is integral with the distillation column in step 1, to distil methyl acetate, methanol, water and entrainer out of the reaction mixture. Thus, at atmospheric pressure, suitable reaction temperatures are in the range of from 90 to 150° C., preferably from 95 to 125° C. To achieve the elevated temperature, the reaction vessel may be provided with, for example, steam coils, or other forms of heating.

To ensure an efficient separation of the overhead product fraction containing water within an optimal concentration, the overall pressure (such as the head pressure) of the distillation column of step 1 is at most 5 bara, preferably at most 3 bara, more preferably at most 2 bara. As used throughout the present disclosure, the term "overall pressure" may include, or be replaced by, the term "head pressure," particularly in respect of step 1 of the process of the present invention.

Preferably, reflux is provided to the distillation column of step 1 by condensing at least a portion, preferably all, of an overhead fraction of the distillation column of step 1 in a condenser and returning a portion of the condensate to the distillation column of step 1 (primary reflux), the remainder of the overhead fraction (remaining condensate and optionally uncondensed overhead fraction) being the overhead product fraction. The primary reflux ratio may suitably be in the range of from 1:2 to 10:1, preferably from 1:1 to 10:1, more preferably from 1:1 to 5:1 (defined as the ratio of reflux flow rate to distillate flow rate).

Based on operating the distillation column of step 1 at atmospheric pressure, the sidestream fraction is preferably removed from the distillation column of step 1 at a point in the column at which the column temperature is in the range of from 70 to 120° C., such as in the range of from 70 to 90° C.; depending upon the actual pressure under which the distillation column of step 1 is operating, the point at which the sidestream would be removed from the column may be at a higher or lower temperature range, suitable temperature ranges would be readily calculated by a skilled person. In terms of theoretical stages, this point should be not less than 5 and preferably not less than 10 theoretical stages from the base of the distillation column. In addition to water, methanol, methyl acetate and entrainer, the liquid sidestream fraction may optionally also contain ethyl acetate.

From the liquid sidestream fraction, a fraction comprising the majority of the methanol, entrainer and methyl acetate, may suitably be separated from a fraction comprising the majority of the water. By the term "fraction comprising the majority of the methanol, entrainer and methyl acetate", it is meant that said fraction comprises at least 50 mol %, preferably at least 60 mol %, more preferably at least 70 mol %, of the total amount of methanol, entrainer and methyl acetate in the liquid sidestream fraction that is separated. By the term "fraction comprising the majority of the water", it is meant that said fraction comprises at least 50 mol %, preferably at least 60 mol %, more preferably at least 70 mol %, of the total amount of water in the liquid sidestream fraction that is separated. The separation of a fraction comprising the majority of the methanol, entrainer and methyl acetate from a fraction comprising the majority of the water may suitably be performed by decantation, wherein the fraction comprising the majority of the methanol, entrainer and methyl acetate forms an upper organic phase and is separated from a lower aqueous phase comprising the fraction comprising the majority of the water. Preferably, the separation of a fraction comprising the majority of the methanol, entrainer and methyl acetate from a fraction comprising the majority of the water may suitably be performed by optionally cooling the liquid sidestream such that it separates more effectively into an organic phase which consists of the fraction comprising the majority of the methanol, entrainer and methyl acetate and an aqueous phase which consists of the fraction comprising the majority of the water, and the organic phase and aqueous phase being separated by decantation. The fraction comprising the majority of the methanol, entrainer and methyl acetate is preferably returned to the esterification reaction vessel or another suitable point in the esterification system, such as the distillation column of step 1 or by being mixed with the lower boiling product stream recycled in step 7, more preferably it is returned to a point in the distillation column of step 1 which is lower than the sidestream fraction removal point. The fraction comprising the majority of the water may be disposed of, or may optionally be subjected to further steps to recover any methanol, entrainer, methyl acetate and optionally ethyl acetate present therein; optionally, said recovered methanol, entrainer, methyl acetate and optionally ethyl acetate may be returned to the esterification reaction vessel or another suitable point in the esterification system, such as the distillation column of step 1 or by being mixed with the lower boiling product stream recycled in step 7. If the fraction comprising the majority of the water is subjected to further steps to recover any methanol, entrainer, methyl acetate and optionally ethyl acetate present therein, at least a portion of the remaining water from said fraction is disposed of in a suitable manner, optionally a portion of said water may be returned back to the decanter.

In the embodiment wherein a fraction comprising the majority of the methanol, entrainer and methyl acetate is separated from the liquid sidestream fraction by decantation, the molar ratio of acetic acid to methanol in the esterification reaction vessel has to be maintained within a suitable range to ensure that the sufficient phase split occurs.

Increasing the methanol to acetic acid ratio in the esterification reaction vessel, for instance to control the amount of water present in the overhead product fraction, will result in an increasing amount of methanol present in the vicinity of the distillation column at which the liquid sidestream is removed, this increasing amount of methanol may result in a weakening in the liquid phase separation in the liquid sidestream so that the water may not be as effectively removed from the esterification reaction vessel. In instances wherein the liquid phase separation in the liquid sidestream occurs, additional entrainer and/or water may be added to the liquid sidestream to provide a greater degree of liquid phase separation.

The distillation column may suitably incorporate means for facilitating the removal of a liquid sidestream fraction which means may take the form of a deep weir or chimney tray located immediately below the point in the distillation column of step 1 from which the sidestream fraction is removed. Using such means it may be possible to maximise the concentration of water in the sidestream fraction by facilitating phase separation within the column.

To replace any entrainer lost overhead or in the fraction comprising the majority of the water, additional entrainer may be fed to the esterification reaction vessel.

The entrainer may be any hydrocarbon, ether, ester, ketone, or mixture thereof, which is sparingly soluble in water and which forms a minimum boiling point azeotrope with water. Examples of suitable entrainers are toluene, diisobutyl ether, butyl acetate (n-butyl acetate, iso-butyl acetate, or mixtures thereof) and methyl isobutyl ketone. Thus, in one embodiment of the present invention, the entrainer is selected from toluene, diisobutyl ether, n-butyl acetate, iso-butyl acetate, methyl ethyl ketone, and mixtures thereof. Preferably, the entrainer is an acetic acid ester, such as n-butyl acetate. In the embodiment wherein the entrainer is an acetic acid ester, the entrainer may added to the esterification reaction vessel and/or the distillation column of step 1 as the acetic acid ester, or, alternatively, the ester may be formed in situ by adding the component alcohol, such as n-butanol when n-butyl acetate is used as the entrainer, to the esterification reaction vessel. Preferably, the entrainer is selected from a butyl acetate, more preferably n-butyl acetate.

The amount of entrainer present in the esterification reaction vessel may suitably be greater than 1 wt %, preferably from 1 to 25 wt %, based on the total contents of the esterification reaction vessel.

The esterification catalyst may be any known esterification catalyst which is suitable for use in the esterification of acetic acid with methanol in an esterification reaction vessel as described above.

Known esterification catalysts include mineral acids, such as hydrochloric acid and sulphuric acid; organic acids, such as organic sulphonic acids (e.g. para-toluene sulphonic acid and alkyl sulphonic acids, such as methane sulphonic acid); tin-based catalysts, such as di-butyl tin oxide; and, solid esterification catalysts, such as acidic zeolites, supported heteropolyacids and ion-exchange resins.

In one particular embodiment of the present invention, the esterification catalyst used in step 1 of the process of the present invention is a homogeneous catalyst. In this embodiment, the esterification catalyst used in step 1 of the process of the present invention is preferably selected from sulphuric acid, and organic sulphonic acids; more preferably, the esterification catalyst used in step 1 of the process of the present invention is an organic sulphonic acid; most preferably, the esterification catalyst used in step 1 of the process of the present invention is selected from para-toluene sulphonic acid and methane sulphonic acid. In one specific embodiment of the present invention, the esterification catalyst used in step 1 of the process of the present invention is methane sulphonic acid.

In one particular embodiment of the present invention, the esterification catalyst used in step 1 of the process of the present invention is selected from sulphuric acid and organic sulphonic acids, and the esterification catalyst is present in the esterification reaction vessel of step 1 in an amount in the range of from 0.1 to 10 wt %, preferably from 0.5 to 8 wt %, more preferably from 1 to 6 wt %, most preferably from 2 to 5 wt %, based on the weight of esterification catalyst adjusted to the equivalent weight of methane sulphonic acid relative to the total weight of the reaction mixture.

In the embodiment of the present invention wherein the esterification catalyst is methane sulphonic acid, the methane sulphonic acid esterification catalyst may suitably be present in the esterification reaction vessel of step 1 in an amount in the range of from 0.1 to 10 wt %, preferably from 0.5 to 8 wt %, more preferably from 1 to 6 wt %, most preferably from 2 to 5 wt %, based on the total weight of the reaction mixture.

The reaction mixture may also optionally contain a suitable amount of corrosion inhibitor, preferably between 0.1 and 1 wt % based on the total weight of the reaction mixture, to reduce corrosion of the vessel. A preferred corrosion inhibitor that may be used is copper in the form of a salt which is soluble in the reaction mixture and would not adversely affect the esterification reaction, for example copper acetate.

The source of acetic acid that is fed to the esterification reaction vessel of step 1 is not limited and any suitable source of acetic acid may be used. Non-limiting examples of processes suitable for the preparation of acetic acid include methanol carbonylation, acetaldehyde oxidation, ethylene oxidation, oxidative fermentation, and anaerobic fermentation.

A particularly suitable source of acetic acid that may be fed to the esterification reaction vessel of step 1 may be derived from the carbonylation of methanol and/or its reactive derivatives in the presence of a suitable catalyst. Processes for producing acetic acid by the Group VIII metal catalysed, hydrocarbyl halide co-catalysed carbonylation of alcohols and/or their reactive derivatives, in particular methanol and/or its reactive derivatives, are well-known in the art. Representative of such art employing rhodium as the Group VIII noble metal catalyst may be mentioned, for example, U.S. Pat. No. 3,772,380; GB-A-1468940; GB-A-1538783 and EP-A-0087070. Representative of such art using iridium as the Group VIII noble metal catalyst may be mentioned, for example, GB-A-1234121; U.S. Pat. No. 3,772,380; DE-A-1767150; EP-A-0616997; EP-A-0618184; EP-A-0618183; and EP-A-0657386. Optionally, the process for the production of ethanol may be integrated with such methanol carbonylation processes.

Thus, according to one aspect of the present invention, the acetic acid fed to the esterification reaction vessel of step 1 may be prepared from a methanol stream, together with carbon monoxide, in a carbonylation reaction. The methanol used in such carbonylation reactions is preferably prepared by a methanol synthesis reaction from synthesis gas, however said methanol stream may also emanate from another suitable source, such as a bio-fermentation process and/or pyrolysis (e.g. wood pyrolysis). Processes for the synthesis of methanol from synthesis gas are well known in the art.

Thus, in specific embodiments of the present invention, it is possible to derive some or all of the reactants in the process of the present invention from synthesis gas. For example, the acetic acid may be formed from methanol and carbon monoxide, both of which may be derived from synthesis gas, as may the methanol used in the esterification reaction vessel of step 1 and the hydrogen in the hydrogenation unit of step 2. The process by which the synthesis gas may be formed is not limited, and a number of processes for the preparation of synthesis gas are well known in the art. The synthesis gas may conveniently be obtained from a variety of carbonaceous feedstock sources, non-limiting examples of suitable carbonaceous feedstock sources include natural gas, oil, petroleum, coal, coke, biomass, municipal waste, and combinations thereof.

The carbon monoxide used in the carbonylation reaction may suitably be obtained by separation of synthesis gas and, when the methanol used in the carbonylation reaction is derived from a methanol synthesis process from synthesis gas, at least part of the carbon monoxide is preferably obtained from the same source of synthesis gas used to produce the methanol. Methods of obtaining a carbon monoxide stream suitable for use in methanol carbonylation processes from synthesis gas are well known in the art.

Similarly, the hydrogen used in the hydrogenation unit of step 2 may suitably be obtained by separation of synthesis gas and, in the embodiments of the present invention wherein the acetic acid is obtained from the carbonylation of methanol, at least part of the hydrogen for the hydrogenation unit of step 2 and at least part of the carbon monoxide used for the carbonylation of methanol may be obtained by separation of synthesis gas. Methods of separating hydrogen and carbon monoxide from synthesis gas are well known in the art.

The majority of the methanol that is fed to the esterification reaction vessel of step 1 is from the recycle of the lower boiling product stream from step 6, preferably at least 80 mol %, more preferably at least 85 mol %, even more preferably at least 90 mol %, most preferably at least 95 mol %, of the methanol that is fed to the esterification reaction vessel of step 1 is from the recycle of the lower boiling product stream from step 6. Additional methanol may be added to the esterification reaction vessel of step 1 in order to maintain the desired molar ratio of acetic acid to methanol in the esterification reaction vessel. The source of any additional methanol that may be added to the esterification reaction vessel of step 1 is not limited and any suitable source of methanol may be used.

It would be understood by the skilled person that during the initial start-up of the process of the present invention, the recycle stream of step 7 will not be able to provide the original charge of methanol. The source of the original charge of methanol in the esterification reaction vessel of step 1 is not limited and any suitable source of methanol may be used. Preferably, methanol from the same source may be used as the original charge of methanol and any additional methanol that may be added to the esterification reaction vessel of step 1.

Conveniently, if the acetic acid which is fed to the carbonylation reaction vessel of step 1 is obtained from the carbonylation of methanol, the methanol from the same source as used in the preparation of the acetic acid may be used as the additional methanol and the original charge of methanol in the process of the present invention.

The process of the present invention results in very low levels of ethyl acetate being fed to the esterification reaction vessel through the recycle stream of step 7 due to the high conversion of methyl acetate to methanol and ethanol in the hydrogenation unit of step 2 and the separation of step 6. Advantageously, because very low levels of ethyl acetate are present in the esterification reaction vessel of step 1, the amount of water present in the overhead product fraction can be controlled to be within the desired range without the need to add methanol in amounts exceeding the acetic acid to methanol ratio of 1:1.8; advantageously, this enables the liquid sidestream fraction withdrawn from an intermediate point in the distillation column of step 1 to be more easily separated into an aqueous stream and an organic stream which may be recycled.

Thus, in one particular embodiment, the process of the present invention can also be used to provide a process for the production of ethanol from methanol, carbon monoxide and hydrogen, said process comprising the following steps:
(a) reacting methanol together with carbon monoxide in the presence of a suitable methanol carbonylation catalyst system to produce acetic acid;
(b) proceeding with a process according to steps 1 to 7 and optionally 8 of the present invention, wherein acetic acid used in step 1 of the process is the acetic acid produced in step (a) above.

Preferably, in the embodiment wherein the process of the present invention is used to provide a process for the production of ethanol from methanol, carbon monoxide and hydrogen, the methanol used in step 1 of the process is obtained from the same source as the methanol used in step (a).

Preferably, in the embodiment wherein the process of the present invention is used to provide a process for the production of ethanol from methanol, carbon monoxide and hydrogen, the methanol used in step 1 of the process is obtained from synthesis gas by a methanol synthesis reaction. More preferably, in this embodiment, the hydrogen for the hydrogenation unit of step 2 and the carbon monoxide used for the carbonylation of methanol are obtained by separation of synthesis gas obtained from the same source as that used for the methanol synthesis reaction.

Through the use of the esterification system described in step 1 of the process of the present invention, the overhead product fraction comprising methyl acetate, methanol and water from step 1 comprises from 0.5 to 5 mol % water. It has been found that maintaining the water concentration in such a range is beneficial to the hydrogenation of methyl acetate over a copper based hydrogenation catalyst. In particular, a concentration of water in the specified range can provide benefits in terms of productivity and selectivity; additionally, concentrations of water in the specified range may also limit the production of ethyl acetate through trans-esterification in the hydrogenation unit and subsequently reduce the amount of ethyl acetate that may be recycled to the esterification reaction vessel of step 1 through the recycle stream of step 7.

In a specific embodiment of the process of the present invention, the overhead product fraction comprising methyl acetate, methanol and water from step 1, is vaporised prior to being fed to the hydrogenation unit in step 2. The means by which the vaporisation of the overhead product fraction comprising methyl acetate, methanol and water from step 1 is performed is not limited and any suitable means known in the art may be used.

Advantageously, the process of the present invention provides a process wherein it is not necessary to add water to the methyl acetate stream which is being passed to the hydrogenation unit of step 2. Thus, in a particularly preferred embodiment of the process of the present invention, all of the overhead product fraction comprising methyl acetate, methanol and water from step 1, is passed directly to a means for vaporising said fraction and vaporised overhead product fraction comprising methyl acetate, methanol and water is fed directly from the vaporising means to the hydrogenation unit in step 2.

In step 2 of the process of the present invention, the overhead product fraction comprising methyl acetate, methanol and water from step 1, is fed together with hydrogen, into a hydrogenation unit containing a copper based hydrogenation catalyst, wherein said hydrogenation unit is operated in the vapour phase at elevated temperature, preferably at a temperature in the range of from 180 to 270° C., and elevated pressure, preferably in the range of from 20 to 100 bara, to produce a hydrogenation product stream comprising ethanol, methanol, unreacted methyl acetate, unreacted hydrogen, water and ethyl acetate, wherein the total molar ratio of hydrogen to methyl acetate in the hydrogenation unit is in the range of from 5:1 to 20:1.

Preferably, the hydrogenation unit of step 2 of the process of the present invention is operated at high conversion of methyl acetate to ethanol and methanol; in particularly, the hydrogenation unit is typically operated at a conversion or methyl acetate of at least 75 mol %, more preferably at least 80 mol %, even more preferably at least 85 mol %, and most preferably at least 90 mol %.

Whilst not wishing to be bound by theory, it is believed that the hydrogenation reaction occurring in the hydrogenation is an equilibrium reaction, with methyl acetate reacting with hydrogen to produce methanol and ethanol. Due to the presence of ethanol in the hydrogenation unit, and due to the equilibrium nature of the hydrogenation reaction, some ethyl acetate will be formed in the hydrogenation unit and will be present in the effluent stream from the hydrogenation unit.

The source of the hydrogen gas that is fed to the hydrogenation unit of step 2 is not limited and any suitable source of hydrogen may be used.

In the hydrogenation unit of step 2, the total molar ratio of hydrogen to methyl acetate in the hydrogenation unit is in the range of from 5:1 to 20:1.

The hydrogenation unit of step 2 may consist of a single reactor or may comprise two or more reactors; if the hydrogenation unit comprises two or more reactors, the reactors may be arranged in series, in parallel, or a combination thereof. The reactor or reactors of the hydrogenation unit may be adiabatic or reactors incorporating heat removal means.

In the embodiments wherein two or more reactors are used in series, heat exchangers and/or intercoolers and/or additional reactant and/or recycle of intermediates can be employed in between successive reactors to control the reaction temperature.

In one specific embodiment of the present invention, the hydrogenation unit of step 2 comprises one or more reactors incorporating heat removal means, preferably one or more multi-tubular reactors.

In another specific embodiment of the present invention, the hydrogenation unit of step 2 comprises one or more adiabatic reactors. In this embodiment of the present invention, the hydrogenation unit preferably comprises two or more adiabatic reactors connected in series, more preferably from 2 to 12 adiabatic reactors connected in series, even more preferably from 3 to 10 adiabatic reactors connected in series, most preferably from 4 to 8 adiabatic reactors connected in series. Preferably, the temperature rise in a single adiabatic reactor is no more than 50° C., more preferably in the range of from 5 to 50° C., and most preferably in the range of from 10 to 25° C. The adiabatic reactors in a series of adiabatic reactors may be operated at different temperatures depending on composition of the individual reactor feeds in order to optimise conversion of methyl acetate to methanol and ethanol.

In another specific embodiment of the present invention, the hydrogenation unit of step 2 comprises two or more adiabatic reactors connected in series, wherein all of the hydrogen is fed to the first adiabatic reactor and part of the overhead product fraction from step 1 is fed to the first adiabatic reactor and the remaining part(s) of the overhead product fraction from step 1 is fed to the inlet of the second and/or subsequent adiabatic reactor(s) together with the effluent of the previous adiabatic reactor in the hydrogenation unit.

In another specific embodiment of the present invention, the hydrogenation unit of step 2 comprises two or more adiabatic reactors connected in series, wherein part of the hydrogen is fed to the first adiabatic reactor with the remaining part(s) of the hydrogen being fed to the subsequent adiabatic reactor(s), and part of the overhead product fraction from step 1 is fed to the first adiabatic reactor and the remaining part(s) of the overhead product fraction from step 1 is fed to the inlet of the second and/or subsequent adiabatic reactor(s) together with the effluent of the previous adiabatic reactor in the hydrogenation unit.

In another specific embodiment of the present invention, the hydrogenation unit of step 2 comprises two or more adiabatic reactors connected in series, wherein over 50 mol % of the hydrogen is fed to the first adiabatic reactor with the remaining portion of the hydrogen being fed to the subsequent adiabatic reactor(s), and part of the overhead product fraction from step 1 is fed to the first adiabatic reactor and the remaining part(s) of the overhead product fraction from step 1 is fed to the inlet of the second and/or subsequent adiabatic reactor(s) together with the effluent of the previous adiabatic reactor in the hydrogenation unit.

In another specific embodiment of the present invention, the hydrogenation unit of step 2 comprises two or more adiabatic reactors connected in series, wherein all of the overhead product fraction from step 1 is fed to the first adiabatic reactor and part of the hydrogen is fed to the first adiabatic reactor and the remaining part(s) of the hydrogen is fed to the inlet of the second and/or subsequent adiabatic reactor(s) together with the effluent of the previous adiabatic reactor in the hydrogenation unit.

The hydrogenation unit of step 2 of the process of the present invention contains a copper based hydrogenation catalyst. Preferred copper based hydrogenation catalysts are catalysts comprising copper oxide. When the hydrogenation catalyst is a catalyst comprising copper oxide, at least part of the copper oxide present will be reduced to metallic copper in the hydrogenation unit.

The copper based hydrogenation catalysts used in step 2 of the process of the present invention may be supported on any suitable support known to those skilled in the art; non-limiting examples of such supports include carbon, silica, titania, clays, aluminas, zinc oxide, zirconia and mixed oxides; zinc oxide is a preferred catalyst support. Preferably, when the copper-based catalyst is supported, the amount of copper present on the catalyst is in the range of from 20 to 40 wt % based on the total weight of the catalyst.

In one particular embodiment of the present invention, the copper based hydrogenation catalyst is a catalyst comprising copper oxide on a support, preferably a catalyst comprising copper oxide on a metal oxide catalyst support, more preferably a catalyst comprising copper oxide supported on a zinc oxide support.

In another specific embodiment of the present invention, the copper based hydrogenation catalyst is a catalyst comprising copper oxide and zinc oxide and optionally a catalyst support. In another specific embodiment of the present invention, the copper based hydrogenation catalyst is a catalyst consists of an admixture of copper oxide and zinc oxide.

The hydrogenation unit of step 2 is operated in the vapour phase, that is, the hydrogen, methyl acetate, water, methanol, ethanol and optionally ethyl acetate if present, in the hydrogenation unit are in the vapour phase in the section of the reactor(s) where the hydrogenation reaction is occurring.

The temperature at which the hydrogenation unit of step 2 of the process of the present invention is operated is in the range of from 180 to 270° C., preferably in the range of from 190 to 260° C., more preferably 200 to 260° C. The pressure at which the hydrogenation unit of step 2 of the process of the present invention is operated is in the range of from 20 to 100 bara, preferably in the range of from 30 to 80 bara, more preferably in the range of from 40 to 70 bara.

The hydrogenation unit can be conducted in batch or semi continuous or continuous mode. Continuous mode of operation is the most preferred.

The GHSV for continuous operation is preferably in the range of from 50 to 50,000 $h^{-1}$, more preferably in the range of from 1,000 to 30,000 $h^{-1}$, and most preferably in the range of from 2,000 to 9,000 $h^{-1}$.

The hydrogenation unit of step 2 of the process of the present invention produces a hydrogenation product stream comprising ethanol, methanol, unreacted methyl acetate, unreacted hydrogen, water and ethyl acetate. The amount of ethyl acetate in the hydrogenation product stream produced in step 2 of the process of the present invention is preferably less than 3 mol % based on the total amount of the liquid portion of the hydrogenation product stream, that is, the components in the hydrogenation product stream that are liquid under standard ambient temperature and pressure (25° C. and 1 bara) (herein also referred to as "SATP"); more preferably, the amount of ethyl acetate in the hydrogenation product stream produced in step 2 of the process of the present invention is less than 2 mol % based on the total amount of the liquid portion of the hydrogenation product stream.

In step 3 of the process of the present invention, the hydrogenation product stream from step 2 is cooled to a temperature below 120° C., preferably to a temperature below 80° C., and a pressure which is no more than 10 bar lower than the pressure of the hydrogenation unit, preferably no more than 5 bar lower than the pressure of the hydrogenation unit, such that the majority of the methanol, ethanol, methyl acetate, ethyl acetate and water present in the hydrogenation product stream condense. In one specific embodiment of the present invention, in step 3, the hydrogenation product stream from step 2 is cooled to a temperature below 120° C., preferably to a temperature below 80° C., and a pressure which has a pressure differential from the pressure of the hydrogenation unit of less than 10 bar, preferably less than 5 bar, such that the majority of the methanol, ethanol, methyl acetate, ethyl acetate and water present in the hydrogenation product stream condense. In another specific embodiment of the present invention, in step 3, the hydrogenation product stream from step 2 is cooled to a temperature below 120° C., preferably to a temperature below 80° C., and a pressure which is lower than the pressure of the hydrogenation unit and having a pressure differential from the pressure of the hydrogenation unit of less than 10 bar, preferably having a pressure differential from the pressure of the hydrogenation unit of less than 5 bar, such that the majority of the methanol, ethanol, methyl acetate, ethyl acetate and water present in the hydrogenation product stream condense.

By the term "the majority of the methanol, ethanol, methyl acetate, ethyl acetate and water present in the hydrogenation product stream condense", it is meant that at least 50 mol %, preferably at least 60 mol %, more preferably at least 70 mol %, even more preferably at least 80 mol %, of the methanol, ethanol, methyl acetate, ethyl acetate and water present in the hydrogenation product stream condense.

In step 4 of the process of the present invention, the cooled hydrogenation product stream from step 3 is separated into a liquid phase which comprises the majority of the methanol, ethanol, methyl acetate, ethyl acetate and water, and a gaseous phase which comprises the majority of the unreacted hydrogen. It would be understood by a skilled person that although the gaseous phase would consist of a majority of unreacted hydrogen, minor amounts of all of the components present in the hydrogenation product stream from step 3 would also be present in the gaseous phase as well as any by-products, in particular normally gaseous by-products (i.e. gaseous under SATP), such as methane and/or ethane, that may have been produced in the hydrogenation unit of step 2.

By the term "liquid phase which comprises the majority of the methanol, ethanol, methyl acetate, ethyl acetate and water", it is meant at least 50 mol %, preferably at least 60 mol %, more preferably at least 70 mol %, even more preferably at least 80 mol %, most preferably at least 90 mol %, of the methanol, ethanol, methyl acetate, ethyl acetate and water present in the cooled hydrogenation product stream passed to step 4 are separated into the liquid phase. By the term "gaseous phase which comprises the majority of the unreacted hydrogen", it is meant at least 50 mol %, preferably at least 60 mol %, more preferably at least 70 mol %, even more preferably at least 80 mol %, most preferably at least 90 mol %, of the unreacted hydrogen present in the cooled hydrogenation product stream passed to step 4 are separated into the gaseous phase.

The separation of step 4 may be performed by any suitable means known in the art. For example, the separation of step 4 may be performed in a distillation column or in a flash separation unit. In a preferred embodiment, the separation of step 4 is performed in a flash separation unit.

In step 5 of the process of the present invention, at least part of the gaseous phase from step 4, preferably at least 80 vol. % of the gaseous phase from step 4, more preferably at least 90 vol. % of the gaseous phase from step 4, most preferably at least 95 vol. % of the gaseous phase from step 4, is recycled to the hydrogenation unit of step 2.

In the process of the present invention, all of the gaseous phase from step 4 may be recycled to the hydrogenation unit of step 2, however, a small bleed stream may be withdrawn from the recycle stream to control and/or reduce the build-up of inert components in the hydrogenation unit of step 2.

In one specific embodiment of the process of the present invention, at least 99 vol % of the gaseous phase from step 4 is recycled to the hydrogenation unit of step 2.

In step 6 of the process of the present invention, the liquid phase of step 4 is separated into a lower boiling product stream comprising methanol, methyl acetate and ethyl acetate, and a higher boiling product stream comprising ethanol, water, in a distillation column operated at an overall pressure of at most 5 bara, preferably at most 3 bara.

The separation performed in step 6 of the process of the present invention is preferably performed such that the higher boiling product stream contains less than 1.0 mol % methanol and the lower boiling product stream contains less than 0.5 mol % ethanol.

In one specific embodiment of the process of the present invention, the lower boiling product stream of step 6 contains less than 0.5 mol % ethanol.

In another specific embodiment of the process of the present invention, the higher boiling product stream of step 6 contains less than 1.0 mol % methanol.

In step 7 of the process of the present invention, at least part of the lower boiling product stream from step 6, preferably at least 80 vol. % of the lower boiling product stream from step 6, more preferably at least 90 vol. % of the lower boiling product stream from step 6, most preferably at least 95 vol. % of the lower boiling product stream from step 6, is recycled to the esterification reaction vessel of step 1.

In the process of the present invention, all of the lower boiling product stream from step 6 may be recycled to the esterification reaction vessel of step 1, however, a small bleed stream may be withdrawn from the recycle stream to control the amount of ethyl acetate and/or ethanol being introduced to the esterification reaction vessel of step 1.

Optionally, an additional water removal step, step 8, may be performed on the higher boiling product stream of step 6 in order to remove water from the ethanol product of the process of the present invention. Conveniently, by use of a process comprising optional step 8, ethanol streams suitable for use in gasoline or for use as a chemical feedstock or solvent, may be conveniently prepared.

EXAMPLES

Catalyst

The catalyst used in these Examples was Pricat™ CZ 29/2T (supplied by Johnson Matthey), which has the following composition: CuO (35 wt %), ZnO (65 wt %).

Catalyst Testing

The catalyst testing experiments were carried out in a pressure flow reactor. The catalyst was heated to 100° C. under a flow of 5 mol % $H_2$ in $N_2$ at 2.5 MPa and a GHSV of 6000 $h^{-1}$. The concentration of $H_2$ was increased in stages to 10, 20, 40, 70 and 100 mol % with a 1 h dwell time at each stage. The catalyst was heated at 1° C./min to a holding temperature of 180° C. and was held for a dwell time of 24 h. At this point catalyst activation was considered complete.

Example 1

A mixture of $H_2$ (90.9 vol %), methyl acetate (8.65 vol %) and water (0.45 vol %) was passed over Pricat CZ 29/2T at 200° C., with a pressure of 5 MPa and a GHSV of 4500 $h^{-1}$ for 18 h. The concentration of water in the ester feed was 5 mol %. The results for Example 1 are given in Table 1. Productivity is defined as kilograms of ethanol plus kilograms of the ethyl portion of ethyl acetate produced per kilogram of catalyst per hour (kg/$kg_{cat}$/h). The relative molar concentrations of methanol, ethanol, methyl acetate and ethyl acetate present in the liquid portion (under SATP) of the product composition, excluding water, is also provided in Table 1.

Example 2

A mixture of $H_2$ (90.9 vol %), methyl acetate (8.87 vol %) and water (0.23 vol %) was passed over Pricat CZ 29/2T at 200° C., with a pressure of 5 MPa and a GHSV of 4500 $h^{-1}$ for 20 hours. The concentration of water in the ester feed was 2.5 mol %. The results for Example 1 are given in Table 1. Productivity is defined as kilograms of ethanol plus kilograms of the ethyl portion of ethyl acetate produced per kilogram of catalyst per hour (kg/$kg_{cat}$/h). The relative molar concentrations of methanol, ethanol, methyl acetate and ethyl acetate present in the liquid portion (under SATP) of the product composition, excluding water, is also provided in Table 1.

Example A—Comparative Example

A mixture of $H_2$ (90.9 vol %) and methyl acetate (9.1 vol %) was passed over Pricat CZ 29/2T at 200° C., with a pressure of 5 MPa and a GHSV of 4500 $h^{-1}$ for 20 h. The results for Example 1 are given in Table 1. Productivity is defined as kilograms of ethanol plus kilograms of the ethyl portion of ethyl acetate produced per kilogram of catalyst per hour (kg/$kg_{cat}$/h). The relative molar concentrations of methanol, ethanol, methyl acetate and ethyl acetate present in the liquid portion (under SATP) of the product composition, excluding water, is also provided in Table 1.

TABLE 1

Results for Examples 1 and 2 and Comparative Example A.

| Example | Water concentration in ester feed (mol %) | Productivity kg/$kg_{cat}$/hr | Conversion (%) | Methanol (mol %) | Ethanol (mol %) | Methyl acetate (mol %) | Ethyl acetate (mol %) |
|---|---|---|---|---|---|---|---|
| 1 | 5 | 0.46 | 87.1 | 46.52 | 46.25 | 4.69 | 2.54 |
| 2 | 2.5 | 0.53 | 97.3 | 47.82 | 50.74 | 0.88 | 0.55 |
| A | 0 | 0.41 | 70.5 | 44.95 | 37.08 | 12.05 | 5.92 |

The results presented in Table 1 demonstrate that maintaining the water within the desired concentration increases the conversion of the methyl acetate to methanol and ethanol and also reduces the concentration of ethyl acetate compared to when water concentrations outside the claimed range are used. Advantageously, the reduction in the relative concentration of ethyl acetate in the hydrogenation product stream would minimise the amount of ethyl acetate which is recycled to the esterification reaction vessel and thus enable the operation of the esterification reaction and associated distillation such that the amount of methanol added to the esterification reaction vessel is maintained within a range to control the amount of water present in the overhead product fraction from the esterification step to within the desired water concentration and also allow liquid separation in the liquid sidestream and consequentially permit continuous removal of water from the esterification reaction.

The invention claimed is:

1. A process for the production of ethanol from acetic acid and hydrogen, said process comprising the following steps:
    (1) reacting in an esterification reaction vessel methanol at elevated temperature with acetic acid in the presence of an esterification catalyst and an entrainer which is sparingly soluble in water and which forms a minimum boiling point azeotrope therewith to form a product comprising entrainer, methyl acetate and water, and in a distillation column, recovering from the product an overhead product comprising methyl acetate, methanol and water, and from an intermediate point in the column removing a liquid sidestream fraction comprising water, methanol, entrainer and methyl acetate, wherein the molar ratio of acetic acid to methanol in the esterification reaction vessel is in the range of from 1:1.1 to 1:1.8, and the distillation column is operated at an overall pressure of at most 5 bara, and wherein the amount of water present in the overhead product fraction comprising methyl acetate, methanol and water is in the range of from 0.5 to 5 mol %;
    (2) feeding the overhead product fraction comprising methyl acetate, methanol and water form step 1, together with hydrogen, into a hydrogenation unit containing a copper based hydrogenation catalyst, wherein said hydrogenation unit is operated in the vapour phase at a temperature in the range of from 180 to 270° C., and a pressure in the range of from 20 to 100 bara, to produce a hydrogenation product stream comprising ethanol, methanol, unreacted methyl acetate, unreacted hydrogen, ethyl acetate and water, wherein the total molar ratio of hydrogen to methyl acetate in the hydrogenation unit is in the range of from 5:1 to 20:1;
    (3) cooling the hydrogenation product stream from step 2 to a temperature below 120° C. and a pressure which is no more than 10 bar lower than the pressure of the hydrogenation unit, such that the majority of the methanol, ethanol, methyl acetate, ethyl acetate and water present in the hydrogenation product stream condense;
    (4) separating the cooled hydrogenation product stream form step 3 into a liquid phase which comprises the majority of the methanol, ethanol, methyl acetate, ethyl acetate and water, and a gaseous phase which comprises the majority of the unreacted hydrogen;
    (5) recycling at least part of the gaseous phase from step 4 to the hydrogenation unit of step 2;
    (6) separating a lower boiling product stream comprising methanol, methyl acetate and ethyl acetate, and a higher boiling product stream comprising ethanol, water, from the liquid phase of step 4 in in a distillation column operated at an overall pressure of at most 5 bara; and
    (7) recycling at least 80 vol % of the lower boiling product stream from step 6 to the esterification reaction vessel of step 1.

2. A process according to claim 1, wherein in step 1, a fraction comprising the majority of the methanol, entrainer and methyl acetate in the sidestream fraction is separated from the water, and the fraction comprising the majority of the methanol, entrainer and methyl acetate is returned to a point in the distillation column of step 1 which is lower than the sidestream fraction removal point.

3. A process according to claim 1, wherein in step 1, the esterification reaction vessel is a kettle at the base of the distillation column.

4. A process according to claim 1, wherein in step 1, the distillation column contains from 15 to 50 theoretical plates.

5. A process according to claim 1, wherein the esterification reaction vessel is operated at a temperature in the range 90 to 150° C.

6. A process according to claim 1, wherein in step 1, primary reflux is provided by condensing an overhead fraction of the distillation column in a condenser and returning a portion of the condensate to the distillation column, wherein the ratio of reflux flow rate to distillate flow rate is in the range of from 1:2 to 10:1.

7. A process according to claim 1, wherein in step 1, the entrainer is selected from toluene, diisobutyl ether, n-butyl acetate, iso-butyl acetate, methyl ethyl ketone, and mixtures thereof.

8. A process according to claim 7, wherein the entrainer is n-butyl acetate.

9. A process according to claim 8, wherein the n-butyl acetate is formed "in-situ" by incorporating n-butanol in the reaction mixture in the esterification reaction vessel.

10. A process according to claim 1, wherein all of the methanol in step 1 is provided by the lower boiling product stream that is recycled in step 7.

11. A process according to claim 1, wherein in addition to the methanol which is provided by the lower boiling product stream that is recycled in step 7, fresh methanol is added to the esterification reaction vessel of step 1.

12. A process according to claim 1, wherein the esterification catalyst in step 1 is a homogeneous catalyst selected from methane sulphonic acid and para-toluene sulphonic acid.

13. A process according to claim 1, wherein the hydrogenation unit of step 2 comprises one or more adiabatic reactors.

14. A process according to claim 13, wherein the hydrogenation unit of step 2 comprises two or more adiabatic reactors connected in series.

15. A process according to claim 14, wherein all of the hydrogen is fed to the first adiabatic reactor and part of the overhead product fraction comprising methyl acetate, methanol and water form step 1 is fed to the first adiabatic reactor and the remaining part(s) of the overhead product fraction comprising methyl acetate, methanol and water is fed to the inlet of the second and/or subsequent adiabatic reactor together with the effluent of the previous adiabatic reactor in the hydrogenation unit.

16. A process according to claim 1, wherein the hydrogenation unit of step 2 comprises at least one multitubular reactor.

17. A process according to claim 1, wherein the separation of step 4 is performed in a flash separation unit.

18. A process according to claim 1, wherein in step 5, at least 99 vol. % of the gaseous phase from step 4 is recycled to the hydrogenation unit of step 2.

19. A process according to claim 1, wherein the lower boiling product stream of step 6 contains less than 0.5 mol % ethanol.

20. A process according to claim 1, wherein the higher boiling product stream of step 6 contains less than 1.0 mol % methanol.

21. A process according to claim 1, wherein the copper based hydrogenation catalyst in step 2 is a catalyst comprising copper oxide.

22. A process according to claim 1, wherein the acetic acid has been prepared by the carbonylation of methanol.

23. A process according to claim 1, wherein the molar ratio of acetic acid to methanol in the esterification reaction vessel of step 1 is within the range of 1:1.2 to 1:1.8.

* * * * *